(12) United States Patent
Cho et al.

(10) Patent No.: US 8,256,273 B2
(45) Date of Patent: *Sep. 4, 2012

(54) DEVICE AND METHOD FOR MEASURING FINE PARTICLE CONCENTRATION

(75) Inventors: Young-Ho Cho, Daejeon (KR); Dong Woo Lee, Busan (KR); Soyeon Yi, Gwangju (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 47 days.

This patent is subject to a terminal disclaimer.

(21) Appl. No.: 12/871,075

(22) Filed: Aug. 30, 2010

(65) Prior Publication Data

US 2010/0319437 A1 Dec. 23, 2010

Related U.S. Application Data

(60) Division of application No. 11/707,665, filed on Feb. 16, 2007, now Pat. No. 7,784,332, which is a continuation of application No. PCT/KR2005/002663, filed on Aug. 16, 2005.

(30) Foreign Application Priority Data

Aug. 17, 2004 (KR) .......................... 10-2004-64723

(51) Int. Cl.
*G01N 15/14* (2006.01)
(52) U.S. Cl. ..................................... 73/61.71
(58) Field of Classification Search ................. 73/23.33, 73/53.01, 61.41, 61.42, 61.71, 865.5; 324/71.4; 356/40

See application file for complete search history.

(56) References Cited

U.S. PATENT DOCUMENTS

| | | | |
|---|---|---|---|
| 3,200,651 A | 8/1965 | Whitehead | |
| 3,449,667 A | 6/1969 | Gourdine | |
| 3,468,607 A | 9/1969 | Onna et al. | |
| 4,030,888 A | 6/1977 | Yamamoto et al. | |
| 4,307,339 A | 12/1981 | Ferrell | |
| 4,447,883 A | 5/1984 | Farrell et al. | |
| 4,457,162 A | 7/1984 | Rush et al. | |
| 5,124,265 A | 6/1992 | Randolph | |
| 5,194,909 A | 3/1993 | Tycko | |
| 5,895,869 A | 4/1999 | Von Behrens et al. | |
| 6,111,398 A | 8/2000 | Graham | |
| 6,175,227 B1 | 1/2001 | Graham et al. | |
| 7,784,332 B2 * | 8/2010 | Cho et al. ..................... 73/61.71 |

OTHER PUBLICATIONS

International Search Report for International Patent Application No. PCT/KR2005/002663, dated Nov. 22, 2005.

* cited by examiner

*Primary Examiner* — John Fitzgerald
(74) *Attorney, Agent, or Firm* — Graybeal Jackson LLP; Kevin D. Jablonski

(57) ABSTRACT

Disclosed is a device for measuring the concentration of the particles contained in a fluid. The device comprises a control volume body having a predetermined effective volume. An inlet path is formed at an end of the control volume body to feed the fluid into the control volume body therethrough. An outlet path is formed at another end of the control volume body to discharge the fluid from the control volume body therethrough. Measuring instruments are provided at the inlet path and the outlet path to emit electrical signals when the fine particles pass through the inlet path and the outlet path. A computing machine receives the electrical signals transmitted from the measuring instruments, and then computes the number and the concentration of fine particles contained in the control volume body. The device is easily integrated with Micro-TAS (Total analysis System).

10 Claims, 3 Drawing Sheets

[FIG. 1]
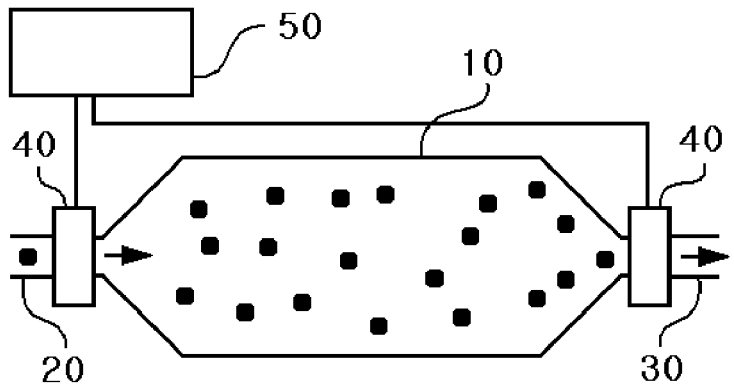
[FIG. 2]
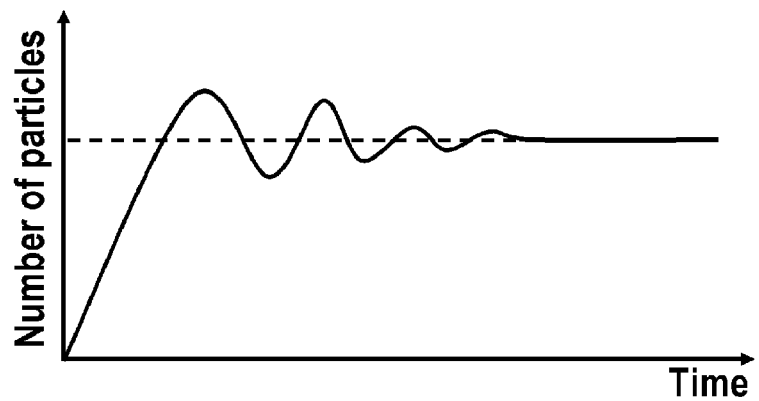
[FIG. 3]
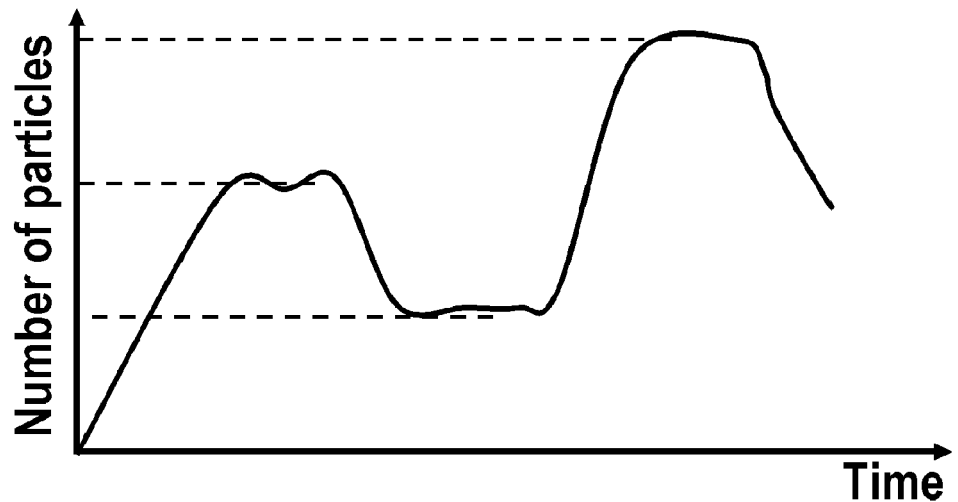

[FIG. 4]
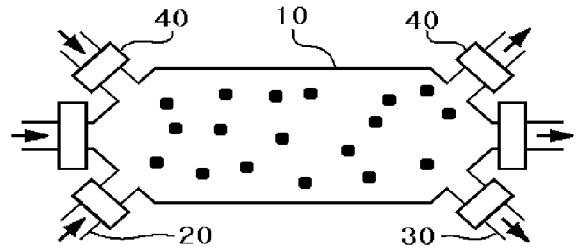
[FIG. 5]
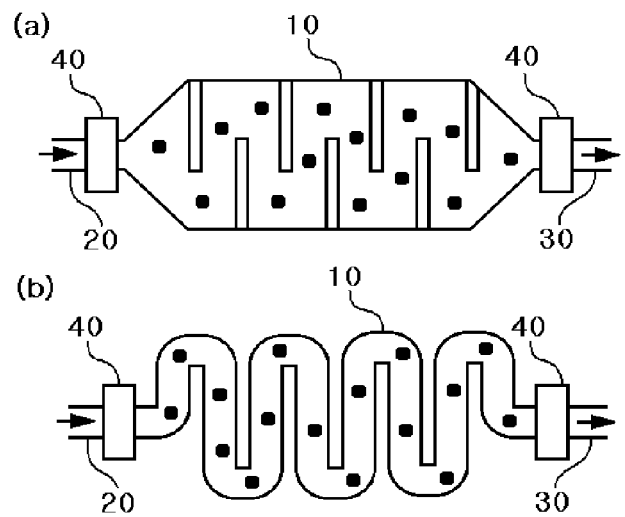
[FIG. 6]
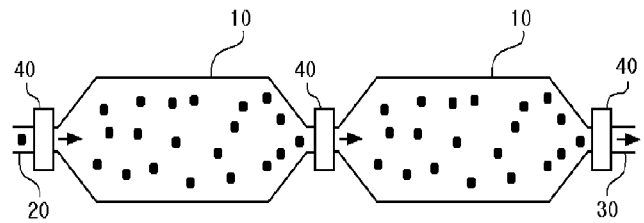
[FIG. 7]
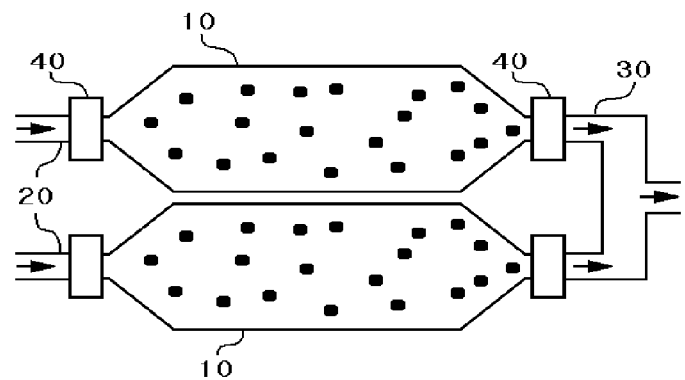

[FIG. 8]
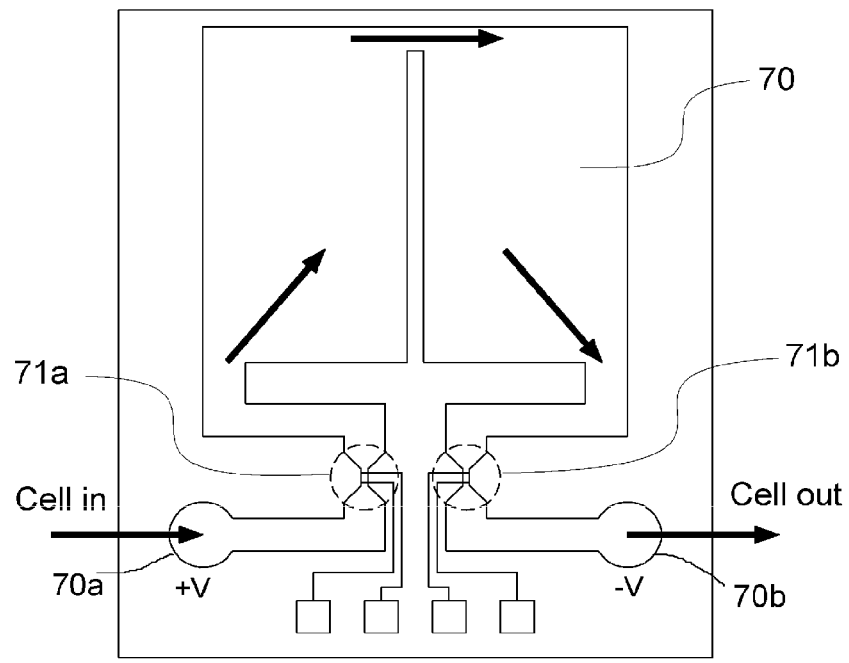
[FIG. 9]
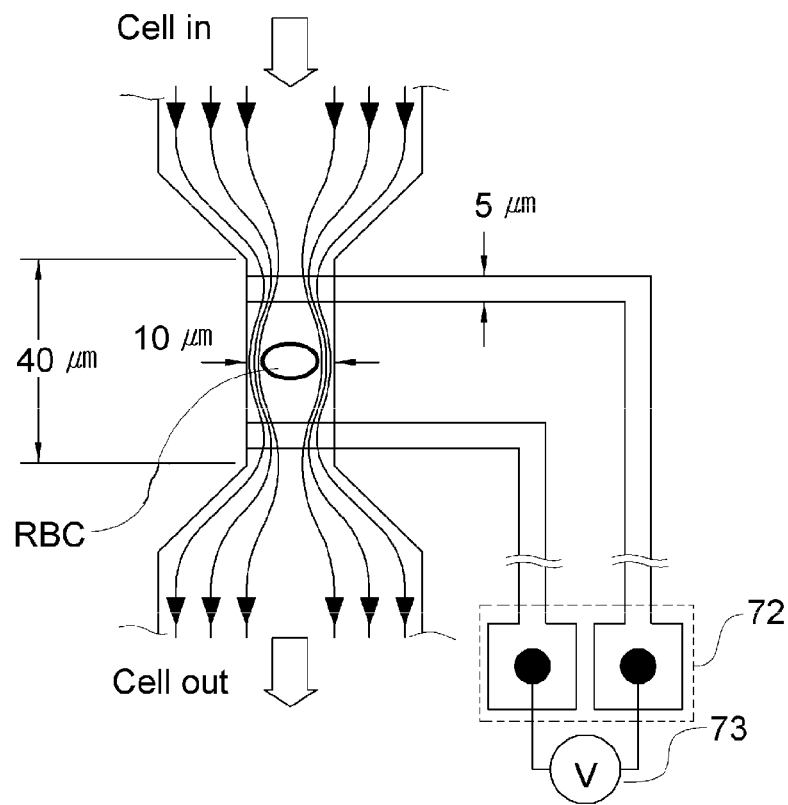

DEVICE AND METHOD FOR MEASURING FINE PARTICLE CONCENTRATION

PRIORITY CLAIM

The present application is a Divisional of U.S. patent application Ser. No. 11/707,665, filed Feb. 16, 2007, currently pending; which is a Continuation application that claims benefit, under 35 USC §120, of co-pending International Application PCT/KR2005/002663, filed Aug. 16, 2005, designating the United States, and that claims foreign priority benefits under 35 USC §119(a) to Korean Patent Application No. 10-2004-0064723 filed Aug. 17, 2004; all of the foregoing applications are incorporated by reference herein in their entireties.

TECHNICAL FIELD

The present invention relates, in general, to a device and a method for measuring a concentration of fine particles contained in a fluid and, more particularly, to a device and a method of measuring a fine particle concentration and a variation of the fine particle concentration, in which the fine particle concentration is precisely measured without a precision flow control pump.

BACKGROUND ART

Generally, measurement of the concentration of fine particles is one of the most frequently conducted procedures in biological, food, and environmental fields. Particularly, a concentration measurement experiment in a medical field is very usefully employed to diagnose patients' health using the number of erythrocytes or leucocytes in the blood. Currently, a Hemacytometer and a Coulter Counter are frequently used as devices for measuring the concentration of fine particles.

The hemacytometer is a device in which a lattice is formed on a glass slide, and the number of fine particles and the volume of the lattice are used to measure a concentration. It is most frequently employed because it has a low-priced chip and a small size. However, this device is disadvantageous in that, since an operator must count the number of fine particles in the lattice one by one using a microscope, precision and efficiency are poor.

The Coulter counter capable of avoiding the disadvantages of the hemacytometer is disclosed in U.S. Pat. Nos. 4,030,888 and 4,307,339. According to the measurement principle of the Coulter counter, the number of fine particles is computed using a change in resistance which is caused by the difference in electrical conductivities of the fine particles and a buffer, and the amount of fluid passing through the buffer is precisely measured to obtain the concentration of fine particles. Hence, the Coulter counter must be equipped with a pump that is capable of transmitting a precise amount of the fluid to the buffer, and it is very important to precisely control the pump. Therefore, the Coulter counter is disadvantageous in that, since the precise pump and many accessories for controlling it are necessary, its price is high.

DISCLOSURE OF INVENTION

Technical Problem

Accordingly, the present invention has been made keeping in mind the above problems occurring in the prior art, and an object of the present invention is to provide a device and a method of measuring a fine particle concentration in a specific region (control volume), in which a difference in numbers of fine particles passing through different inlet paths and outlet paths is calculated without quantitative measurement of a fluid containing the fine particles, thereby the fine particle concentration is easily and precisely measured. Further, real time measurement of the fine particle concentration can be accomplished.

Technical Solution

According to an embodiment of the present invention, there is provided a device for measuring a concentration of fine particles contained in a fluid. The device comprises a control volume body having a predetermined effective volume, an inlet path formed at an end of the control volume body to feed the fluid into the control volume body therethrough, an outlet path formed at another end of the control volume body to discharge the fluid from the control volume body therethrough, measuring instruments provided at the inlet path and the outlet path to emit electrical signals when the fine particles pass through the inlet path and the outlet path, and a computing machine for receiving the electrical signals transmitted from the measuring instruments and computing the number and the real-time concentration of fine particles contained in the control volume body.

According to another embodiment of the present invention, there is provided a method of measuring a concentration of fine particles contained in a fluid. The method comprises a) feeding the fluid containing the fine particles into a tight body having an inlet and an outlet formed therein, b) counting numbers of the fine particles passing through the inlet and the outlet of the tight body, c) calculating a difference in the numbers of fine particles measured in the step b), and d) dividing the difference calculated in the step c) by an effective volume of the tight body to give the concentration of the fine particles.

ADVANTAGEOUS EFFECTS

The present invention is advantageous in that it is possible to precisely and rapidly measure the concentration of fine particles by counting the number of fine particles passing through a space having a known volume without quantitative measurement of a fluid containing the fine particles. Furthermore, the present invention is characterized in that, since a structure is simple and the number of accessories is small unlike a conventional concentration measuring device, it is possible to significantly reduce the size of a device and the production cost. Additionally, in the present invention, since it is possible to miniaturize the device, it can be easily integrated with an integrated system, such as a Micro-TAS (Total Analysis System).

BRIEF DESCRIPTION OF DRAWINGS

FIG. 1 schematically illustrates a device for measuring a fine particle concentration according to an embodiment of the present invention;

FIGS. 2 and 3 are graphs showing a real-time variation in the number of fine particles contained in a control volume body of FIG. 1 under constant concentration and variable concentration, respectively;

FIG. 4 illustrates the control volume body of FIG. 1, which includes a plurality of inlet and outlet paths;

FIGS. 5 (a) and (b) illustrate modifications of the control volume body of FIG. 1;

FIG. 6 illustrates the devices of FIG. 1, which are connected in series; and FIG. 7 illustrates the devices of FIG. 1, which are connected in parallel.

FIG. 8 shows an embodiment of a device for measuring a fine particle concentration according to the present invention.

FIG. 9 is an enlarged scale view of the electrical sensing zone of the device of FIG. 8.

BEST MODE FOR CARRYING OUT THE INVENTION

Hereinafter, a detailed description will be given of preferred embodiments of the present invention, referring to the accompanying drawings.

FIG. 1 schematically illustrates a device for measuring a fine particle concentration according to an embodiment of the present invention, and FIGS. 2 and 3 are graphs showing a change in the number of fine particles contained in a control volume body of FIG. 1 under constant concentration and variable concentration, respectively.

As shown in FIG. 1, the device for measuring a fine particle concentration according to the present invention comprises a control volume body 10, an inlet path 20, an outlet path 30, and measuring instruments 40. The control volume body 10 has an effective voluminal space capable of storing a predetermined amount of fluid therein, and the inlet path 20 and the outlet path 30 are formed on sides of the control volume body 10 so as to be opposite each other. The fluid is fed through the inlet path 20 into the control volume body 10, and is discharged from the control volume body 10 through the outlet path 30. The measuring instruments 40 are provided at the inlet path 20 and the outlet path 30 and emit electrical signals when the fine particles pass through them.

A computing machine 50 connected to the measuring instruments 40 is provided outside the control volume body 10. In the computing machine 50, the number of fine particles passing through the inlet path 20 and the outlet path 30 is computed using the electrical signals emitted from the measuring instruments 40, and the concentration of fine particles contained in the control volume body 10 is computed at real time using the difference in numbers of fine particles transmitted from the measuring instruments 40.

Meanwhile, in the present embodiment, the inlet path 20 and the outlet path 30 each have a sectional area through which a small amount of the fine particles are capable of passing. Theoretically, it is preferable that the sectional areas of the inlet path 20 and the outlet path 30 be similar to the fine particle size in order to monitor the passage of the fine particles with electrical, optical methods. However, if the sectional areas of the inlet path 20 and the outlet path 30 are similar to the size of fine particle, a plurality of fine particles may gather together in the narrow inlet and outlet paths 20, 30, and the particles may be damaged. When using biological cells as an object to be measured, the above-mentioned problem is particularly significant. Therefore, in the present embodiment, it is preferable that the sectional area of the measuring instruments is a few larger than fine particles.

In the present embodiment, the fine particle measuring instruments 40 monitor the passage and the number of fine particles using the difference in impedance that occurs when the fine particles pass therethrough. If a voltage of opposite polarity is applied on the inlet path 20, the impedance of the inlet path 20 has a predetermined value depending on the type of fluid filling the inlet path 20. In connection with this, if impurities, that is, fine particles, are contained in the fluid, the impedance characteristic of the fluid passing through the inlet path 20 varies. In the present embodiment, the passage and number of fine particles are checked using a variation in electrical impedance that occurs when the fine particles pass through the inlet path 20.

Meanwhile, in another embodiment, the passage and the number of fine particles may be monitored using optical properties of the fine particles. Fine particles have intrinsic optical properties (transmissibility, reflectivity, etc.). Hence, if a light source and an optical sensor are provided at the inlet path 20, the intensity of light radiated on the optical sensor depends on the number of fine particles passing through the inlet path 20. An optical measuring instrument for measuring the number of particles monitors the passage and the number of fine particles based on the above description.

According to the present invention, the method of calculating the concentration of fine particles is as follows.

An effective volume of the control volume body 10 is stored in the computing machine 50.

A sufficient amount of fluid is continuously fed into the control volume body 10, the numbers of fine particles passing through the inlet path 20 and the outlet path 30 are computed, and the difference between numbers of fine particles passing through the inlet path 20 and the outlet path 30 is calculated.

The numbers of fine particles passing through the inlet path 20 and the outlet path 30 and the difference thereof are computed by the computing machine 50. In other words, the computing machine 50 checks the numbers of electrical signals that are emitted from the measuring instruments when the fine particles pass through it in the inlet path 20 and the outlet path 30, and independently records the difference in the numbers.

Meanwhile, as shown in FIG. 2, the difference in numbers of fine particles passing through the inlet path 20 and the outlet path 30 continuously increases at an early step. This is because there are no fine particles in the fluid filling the control volume body 10 at the early step. As the fluid containing the fine particles fills the control volume body 10, a difference between the numbers of fine particles passing through the inlet path 20 and the outlet path 30 occurs. From the time when the object fluid filling the control volume body 10 is discharged, the difference between the numbers of fine particles passing through the inlet path 20 and the outlet path 30 becomes constant. The difference between the numbers of fine particles means that some fine particles remain in the control volume body 10 according to the concentration of fine particles in the supplied fluid.

If the supplied concentration of fine particle varies according to time, the difference of the fine particle number in the control volume also varies according to supplied concentration of fine particle. Therefore, in the present invention, the number of the fine particle in the control volume can be monitored at real time.

3) Accordingly, the difference between the numbers of fine particles obtained in step (2) is divided by the value obtained in step 1) to calculate concentration of fine particles per unit volume of fluid at real time.

Meanwhile, by saving and displaying of the fine particle number in the control volume body according to time, the concentration of the fine particle can be monitored at real time.

FIG. 4 illustrates the control volume body of FIG. 1, which includes a plurality of inlet and outlet paths, FIGS. 5 (*a*) and (*b*) illustrate modifications of the control volume body of FIG. 1, FIG. 6 illustrates the devices of FIG. 1 connected in series, and FIG. 7 illustrates the devices of FIG. 1 connected in parallel.

The fine particles contained in the fluid may be biological cells, which are readily damaged by external forces. Hence, the fluid containing the fine particles must be fed into the control volume body 10 at a very low rate. However, if the fluid is fed into the control volume body 10 at the low rate, the time which is required to fill the control volume body 10 with the fluid is increased, thus it takes a long time to conduct measurement. Therefore, in the present embodiment, as shown in FIG. 4, a plurality of inlet paths 20 and a plurality of outlet paths 30 are connected to one control volume body 10 so as to shorten the time required to fill the control volume body 10 with the fluid.

Meanwhile, if the control volume body 10 has one broad open space as shown in FIG. 1, the distribution of fine particles may be nonuniform, causing errors in concentration measurement. That is to say, the fluid flows only at the inlet path 20 and the outlet path 30, but not at an internal surface of the control volume body 10. Hence, the measured concentration of fine particles may be different from the real concentration. Accordingly, in another embodiment, as shown in FIGS. 5 (a) and (b), the control volume body 10 has a maze-shaped structure so that the fluid and the fine particles contained in the fluid do not stay but continuously flow. Modification of the internal shape of the control volume body 10 causes vortexes in the fluid, thereby actively moving the fine particles in conjunction with the fluid.

In the above-mentioned embodiments, one type of fine particle is measured. However, concentrations of various fine particles having different sizes are frequently measured in actual concentration measurement experiments. This problem can be easily solved by the present invention.

Since the electrical impedance that is measured when the fine particles pass through the inlet path 20 and the outlet path 30 is in proportion to the fine particle size, the measuring instruments 40 for measuring the fine particles transmit different electrical signals corresponding to the electrical impedance to the computing machine 50. Accordingly, the electrical signals transmitted to the computing machine 50 are as various as are the type of fine particles. Therefore, if the computing machine 50 has a filtering function of separating the electrical signals in a predetermined bandwidth unit and another function of independently recording and calculating the separated electrical signals, it is possible to simultaneously measure the number and the concentration of different fine particles contained in one fluid.

Meanwhile, if a very small amount of fine particles are contained in the fluid, it is difficult to ensure reliable measurement. For example, if the number of fine particles remaining in the control volume body 10 is 1 or 2, an error in concentration is very high compared to a difference of 1 particle. A method for solving this problem is shown in FIG. 6.

The above-mentioned problem occurs because an effective volume of the control volume body 10 is insufficiently large to precisely express the concentration of fine particles. Thus, if the difference in numbers of fine particles remaining in the control volume body 10 is large as described above, it is necessary to connect a plurality of control volume bodies in series and to count the number of fine particles using values measured at both ends of the resulting control volume body structure 10 so as to increase the effective volume, thereby it is possible to significantly reduce the error in measurement of fine particles.

Conversely, concentration measuring devices may be connected in parallel as shown in FIG. 7. When the devices are connected in parallel, the effective volume and the number of inlet paths 20 simultaneously increase, thus this connection is advantageous in that it is possible to rapidly measure the concentration of fine particles, even if the concentration is very low.

As well, in series and parallel connected device, concentration variation due to some events occurring in each control volume can be measured.

(Embodiment)

The present invention can be applied to a microfluidic device such as cell counter for blood cell concentration measurement.

FIG. 8 shows a red blood cell (RBC) counter using a control volume 70 between double electrical sensing zones 71a and 71b according to an embodiment of the present invention.

Generally, a RBC has a diameter of 7 μm and a height of 2 μm. The electrical sensing zones 71a and 71b according to this embodiment was designated by considering the sizes. As shown in FIG. 9, the height is 10 μm, the width is 10 μm, and the length is 40 μm. Also, Au/Cr electrode 72 having a width 5 μm was built in the electrical sensing zones to measure impedance variation occurred when the RBC passes through the electrical sensing zones. By measuring the impedance variation, the number of the BRC passing through the electrical sensing zones can be measured.

(Another Embodiment)

Meanwhile, at the walls of a channel filled with an electrolyte a charge double-layer will form due to the compensation of fixed charges at the wall by ions in the solution. If at both ends of the channel electrodes are placed and a voltage difference is applied between these electrode, so that an electric field is established in the channel, the charge in the double layer will move, with a velocity and direction depending on the amount and sign of the charge. The moving charge will exert a drag force on the liquid, leading to liquid flow. This flow is called electro-osmotic flow (EOF).

The inventor of the present application applied this EOF effect in this invention.

To generate the EOF effect, in this embodiment, voltage (V) was supplied to the cell in/out ports (70a, 70b) (please see FIG. 9). Then, the RBC will move. That is, a flow of the RBC can be occurred. In this embodiment, it is preferable that the range of the supplied voltage V is about ±15V.

Accordingly, according to this embodiment, if such RBC counter is embodied by integrated on chip, a cell concentration measurement can be performed without an external flow control pump.

Industrial Applicability

Although a device and a method of measuring a fine particle concentration according to the present invention have been disclosed for illustrative purposes in reference to the accompanying drawings, those skilled in the art will appreciate that various modifications, additions and substitutions are possible, without departing from the scope and spirit of the invention as disclosed in the accompanying claims.

For example, the measuring instruments 40, which having a sectional area through which the fluid is passing, can be provided at the inlet path 20 and outlet path 30 so that the fluid passes through the measuring instruments itself.

What is claimed is:

1. A method of measuring a concentration of fine particles contained in a fluid, comprising:
    causing the flow of fluid containing fine particles into a cavity having a volume through an inlet;
    causing the flow of the fluid containing the fine particles out of the cavity through an outlet determining a first number of fine particles passing through the inlet and determining a second number of fine particles passing through the outlet;

calculating a difference between the first number and the second number;

dividing the difference calculated by the volume of the cavity; and determining the concentration of the fine particles based on the division.

2. The method of claim 1, wherein the determining, calculating and dividing is accomplished by a computing device.

3. The method of claim 1, wherein the fine particles in the cavity flow into the cavity through the inlet and out of the cavity through the outlet within an allotted timeframe.

4. The method of claim 1, wherein causing the fluid to flow into the cavity further comprises flowing the fluid into the cavity through a plurality of inlets.

5. The method of claim 1, wherein causing the fluid to flow out of the cavity further comprises flowing the fluid out of the cavity through a plurality of outlets.

6. The method of claim 1, wherein the electrical signal is generated based upon a determined change in an electrical impedance of the fluid in the cavity.

7. The method of claim 1, further comprising facilitating the flow of fluid through the inlet using an electrode at the inlet to supply a voltage that causes the fine particles to flow into the cavity.

8. The method of claim 1, further comprising facilitating the flow of fluid through the outlet using an electrode at the outlet to supply a voltage that causes the fine particles to flow out of the cavity.

9. The method of claim 1, wherein the determining of the numbers of fine particles further comprises generating an electrical signal that depends on sizes of the fine particles such that a computing machine is configured to compute the number of fine particles in the cavity and the concentration of fine particles in the cavity in response to the electrical signals.

10. The method of claim 9, wherein the electrical signal is generated based upon a determined change in an optical property of the fluid in the cavity.

\* \* \* \* \*